United States Patent [19]

Wenzel et al.

[11] Patent Number: 5,538,712
[45] Date of Patent: Jul. 23, 1996

[54] CYCLOPENTADIENYLCARBONYL 99MTC COMPLEXES, PROCESS FOR THEIR PRODUCTION AS WELL AS THEIR USE IN DIAGNOSTICS

[75] Inventors: Martin Wenzel; Paul E. Schulze, both of Berlin, Germany

[73] Assignee: Institut Fur Diagnostikforschung GmbH/an der Freien Universitat Berlin, Berlin, Germany

[21] Appl. No.: 966,183

[22] PCT Filed: May 31, 1991

[86] PCT No.: PCT/DE91/00470

§ 371 Date: Jan. 29, 1993

§ 102(e) Date: Jan. 29, 1993

[87] PCT Pub. No.: WO91/18908

PCT Pub. Date: Dec. 12, 1991

[30] Foreign Application Priority Data

Jun. 1, 1990 [DE] Germany .......................... 40 18 172.3
Sep. 8, 1990 [DE] Germany .......................... 40 28 867.6

[51] Int. Cl.[6] .......................... A61K 51/04; A61K 51/06; C07F 13/00
[52] U.S. Cl. .......................... 424/145; 534/14; 424/165; 424/173
[58] Field of Search .......................... 534/10, 14; 424/1.1, 424/1.65, 1.45, 1.73; 568/379; 556/138, 57

[56] References Cited

U.S. PATENT DOCUMENTS

| 3,028,404 | 4/1962 | Pearson, et al. .......................... 260/429 |
| 4,028,389 | 6/1977 | Wenzel et al. .......................... 260/429 CY |
| 4,584,186 | 4/1986 | Wenzel et al. .......................... 424/1.1 |
| 5,167,948 | 12/1992 | Wenzel .......................... 424/1.1 |

FOREIGN PATENT DOCUMENTS

| 0203815 | 12/1986 | European Pat. Off. . |
| 3218859 | 11/1983 | Germany . |
| 3445782 | 6/1986 | Germany . |
| 3523262 | 1/1987 | Germany . |

OTHER PUBLICATIONS

Chemical Abstracts, Band 60, No. 7, 30 (Mar. 1964), E. O. Fischer et al.: "Aromatic complexes of metals. LXXIII. Acylation of cyclopentadienylrhenium tricarbonyl and cyclopentadienyltechnetiumtricarbonyl", sieh Zusammenfassung No. 8060g, & J. Organometal. Chem. 1(2), 191–9 (1963).

Inorganic Chemistry, Band 15, No. 11 (Nov. 1976), I. G. De Jong et al.: "Radiochemistry of organomolybdenum compounds. 2. formation of technetium compounds by beta–decay in eta–cyclopentadienyltricarbonylmolybdenum", Seiten 2588–2591, siehe den ganzen Artikel; Seite 2591, Registry No. 60184–30–7.

Lukehart, *Fundamental Transition Metal Organometallic Chemistry*, pp. 29–36, 97–101, 1985.

Boag et al., *Comprehensive Organometallic Chemistry*, pages 161 242, 1982.

(List continued on next page.)

Primary Examiner—Shean C. Wu
Assistant Examiner—Lara E. Chapman
Attorney, Agent, or Firm—Millen, White, Zelano & Branigan

[57] ABSTRACT

The invention relates to cyclopentadienylcarbonyl[99mTc] complexes of general formula I

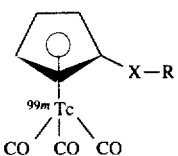
(I)

in which —XR can have various meanings. These new complexes of [99m]technetium can be used in the field of medical diagnosis. The invention further relates to a process for the production of complexes according to the invention.

31 Claims, 5 Drawing Sheets

OTHER PUBLICATIONS

Parker, Spectrochim. Acta., Part A 31A(12), pages 1789–1798, 1975 as abstracted in CA84:73237.

*Dictionary of Organometallic Compounds,* 1984, Techetium entry.

*Journal of Organometallic Chemistry,* vol. 1, No. 2, Fischer et al., 1963, pp. 191–199.

| CYTECTRENE DERIVATIVES WITH SIDE CHAIN X-R | MIN. | MOUSE RAT | RELEVANT CONCENTRATION [% OF THE INJ. DOSE/% OF BODY WEIGHT] | | | | | | SUPRARENAL GLAND | HEART | BRAIN | BRAIN/ BLOOD |
|---|---|---|---|---|---|---|---|---|---|---|---|---|
| | | | MUSCLE | BLOOD | LIVER | LUNG | KIDNEY | | | | | |
| PERTECHNETATE (CONTROL) | 15 | Ms | 0.44 | 2.66 | 1.55 | 1.95 | 1.22 | | 1.63 | 0.86 | 0.09 | 0.03 |
| -COO-⬡N-CH₃ | 15 | R | 0.45 | 0.36 | 4.98 | 5.14 | 5.15 | | — | 0.79 | 1.96 | 5.4 |
| -COO-⬡N-CH₃ | 15 | R | 0.61 | 0.16 | 4.48 | 6.55 | 4.47 | | — | 0.89 | 2.66 | 16.6 |
| -COO-3-QUINUCLIDINOL | 15 | R | 0.64 | 0.32 | 4.19 | 13.8 | 7.01 | | 8.64 | 1.44 | 2.29 | 7.2 |
| -CO-NH-CH₂-COOH | 15 | M | 0.21 | 0.40 | 2.27 | 0.37 | 24.9 | | 0.67 | 1.30 | 0.06 | |
| -CH₂-CH(NH₂)-CH₃ | 15 | Ms | 0.60 | 0.34 | 4.80 | 10.7 | 3.31 | | 4.27 | 1.47 | 1.86 | 5.5 |
| -CO-CH₃ | 15 | Ms | 0.30 | 0.22 | 8.53 | 3.95 | 4.7 | | 8.20 | .019 | 0.10 | |
| -CO-(CH₂)₁₄-COOH | 15 | Ms | 0.16 | 0.33 | 13.8 | 1.52 | 6.01 | | 0.66 | 0.78 | 0.03 | — |
| -CH=TROPINONE | 7,5 | Rt | 0.64 | 0.28 | 3.40 | 8.94 | 4.19 | | 5.34 | 1.54 | 2.63 | 9.4 |

FIG. 5 eluate t = 24h
ether/diethylamine 90:10

F                              Fc reference     S

FIG.6 eluate t = 48h
acetone/EtOH/NH3
95:4:1

F             Fc reference            S

CYCLOPENTADIENYLCARBONYL 99MTC COMPLEXES, PROCESS FOR THEIR PRODUCTION AS WELL AS THEIR USE IN DIAGNOSTICS

SUMMARY OF THE INVENTION

The invention relates to the object characterized in the claims, i.e., cyclopentadienylcarbonyl$^{99m}$Tc complexes, agents containing these complexes, their use as diagnostic agents as well as process for the production of these complexes and agents.

Radioactive metal ions, mostly bound to a complexing agent, have for some time been used for in vivo diagnosis. Among them, technetium-99m ($^{99m}$Tc), because of its almost ideal physical properties for this purpose—good absorption of radiation in corresponding detection devices (gamma camera, SPECT devices) relative to a lower absorption in the human organism and easy availability by a molybdenum/technetium generator—is the radionuclide most often used in clinical nuclear medicine. Its short half-life of 6.02 hours guarantees an only slight exposure of the patient to gamma radiation, particularly since also the daughter nuclide technetium-99 has only a negligible residual radiation. But, a drawback of technetium is its complicated and still not completely known complex chemistry. Technetium can be present in a number of oxidation stages (+7 to −1), which can greatly change the pharmacological properties by changing the charge of a complex. It is therefore necessary to synthesize complexes which bind the technetium in a defined oxidation stage and to prevent redox reactions, which could lead to a redistribution of the pharmaceutical agent. A number of such $^{99m}$Tc complexing agents are already known and are clinically used. In the case of neutral complexes, systems, in which the $^{99m}$Tc is bound between 2–4 nitrogen atoms and 0–2 sulfur atoms ($N_2S_2$, $N_3S$, propylenamine oxime and isonitrile complexes), are often involved. But, often the insufficient stability of these $^{99m}$Tc complexes is a significant drawback (Hung, J. C. et al.; J. Nucl. Med. 29: 1568 [1988]). In clinical use, therefore, e.g., HM-PAO (hexamethyl-propylenamine oxime) has to be administered within 30 minutes after its labeling with $^{99m}$Tc-pertechnetate, so that the amount of by-products, which reduce the diagnostic informative value, does not become too high.

Also, other previously known attempts to couple chelating agents to substances selectively accumulating per se can thus far be considered as unsatisfactory. If functional groups of the complexing agent are used to bind to any low-molecular or polymeric molecule, a weakening of the complex stability often results, i.e., a diagnostically intolerable portion of the radioisotope is released from the conjugate (Brechbiel, M. W. et al., Inorg. Chem. 25: 2772 [1986]) and thus interferes with the physical measurement and as a result the diagnostic value.

In the previously clinically used compounds (e.g., MAG 3 [EP 0250013], ECD [EP 0279417] or HM-PAO [EP 0123504]), the complex, whose exclusive function actually should be to make possible the physical measurement via its γ-radiation, also determines the biological distribution. Thus, these complexes are unsuitable for coupling to low-molecular molecules selectively accumulating in the organism. Further, these complexing agents contain functional groups, which can interact in an undesirable manner with the living organism.

Therefore, there exists an urgent need for stable, easily accessible complexes, which are coupled to various compounds selectively accumulating per se in the organism and whose concentration behavior is determined only by these low-molecular organic molecules.

According to the invention, this object is achieved by compounds of general formula I in which X stands for a carbonyl group or a direct bond, R stands for a phenyl or benzyl radical, or for a saturated or unsaturated, straight-chain or branched $C_{1-16}$ hydrocarbon radical, which optionally contains one to three carbonyl groups and/or one to three carboxy groups and/or a $C_{1-3}$ alkyl, a phenyl or benzylcarboxylic acid ester and/or an $NR_1R_2$ radical, in which $R_1$ and $R_2$ are the same or different and stand for hydrogen, deuterium, a straight-chain or branched $C_{1-6}$ alkyl, a desoxysaccharide or a desaminoergoline radical, or for a —$(CH_2)_l NR_3R_4$ group, in which l=0 or 1 and $R_3$, $R_4$ are the same or different and stand for hydrogen, a straight-chain or branched, saturated or unsaturated $C_{1-6}$ alkyl radical—which is optionally substituted by a $C_{1-3}$ alkyl, phenyl or benzylcarboxylic acid ester or a carboxylic acid radical—or together with the nitrogen atom form a saturated or unsaturated 5- or 6-member ring which optionally contains an oxygen atom or an $NR_5$ or a $CH_5$ group with $R_5$ meaning a hydrogen, deuterium, straight-chain or branched $C_{1-4}$ alkyl radical, or $NR_3R_4$ stands for a 2-nitroimidazole radical or a biogenic amine radical, or for an alcohol molecule reduced by the acid (alcohol) proton, or in which X—R stands for According to the invention, those compounds according to formula I are preferred in which —X—R is —CO—

CH=CH—C₅H₆, —CO—NH—CH₂COOH, —CO—CH₂COOEt, —CO—(CH₂)₂COOH, —CO—(CH₂)₁₄COOH, —CH=CH—CO—CH₃, —CH₂—CH(NH$^{iso}$C₃H₇)CH₃, —CH₂—CH(NH$^{iso}$C₃H₇)C₂H₅, —C≡CH, —CO—C≡CH, —CO—(CH₂)₇COOH, or in which the alcohol radical RO— is a $C_{1-6}$ alkyl, phenyl or benzylalcohol radical, a cyclic amine alcohol, e.g., a cyclic aliphatic aminoalcohol, tropanol, or quinuclidinol, or a steroid alcohol, e.g., 3-cholesterol, 3-estradiol or 17-estradiol radical, or in which the 5- or 6-member ring containing saturated or unsaturated nitrogen, is pyrrole, pyrazole, pyrazine, pyridine, morpholine, pyrrolidine, pyrimidine, piperidine, piperazine, 4-$R_5$-piperidine, N-$R_5$-piperazine, with $R_5$ meaning a straight-chain or branched $C_{1-4}$ alkyl radical, preferably stands for methyl, ethyl, propyl, isopropyl.

As a biogenic amine, there can be mentioned as examples serotonin, histamine, γ-aminobutyric acid.

As an example for a cyclic aliphatic aminoalcohol, there can be mentioned in which $R_6$ stands for the radicals indicated for $R_5$.

Surprisingly, many of the cyclopentadienylcarbonyl$^{99m}$Tc complexes—called in the following cytectrenes—meet the set requirements profile. Thus, the complexes according to the invention exhibit a clearly higher stability relative to the complexes present in the testing, such as, e.g., HM-PAO for brain perfusion. Thus, no $^{99m}$Tc-technetium is released even from metabolites of the administered complexes.

BIOCHEMICAL TESTS

The flexibility of the organ-specificity is to be seen as another advantage of the complexes according to the invention.

The organ distributions in mice and rats as well as partially in rabbits were tested by the technetium-labeled cytectrene derivatives. The organ distribution of the $^{99m}$Tc-labeled cytectrene derivatives is a function of the substituent on the cyclopentadienyl ring system.

Figure 1:
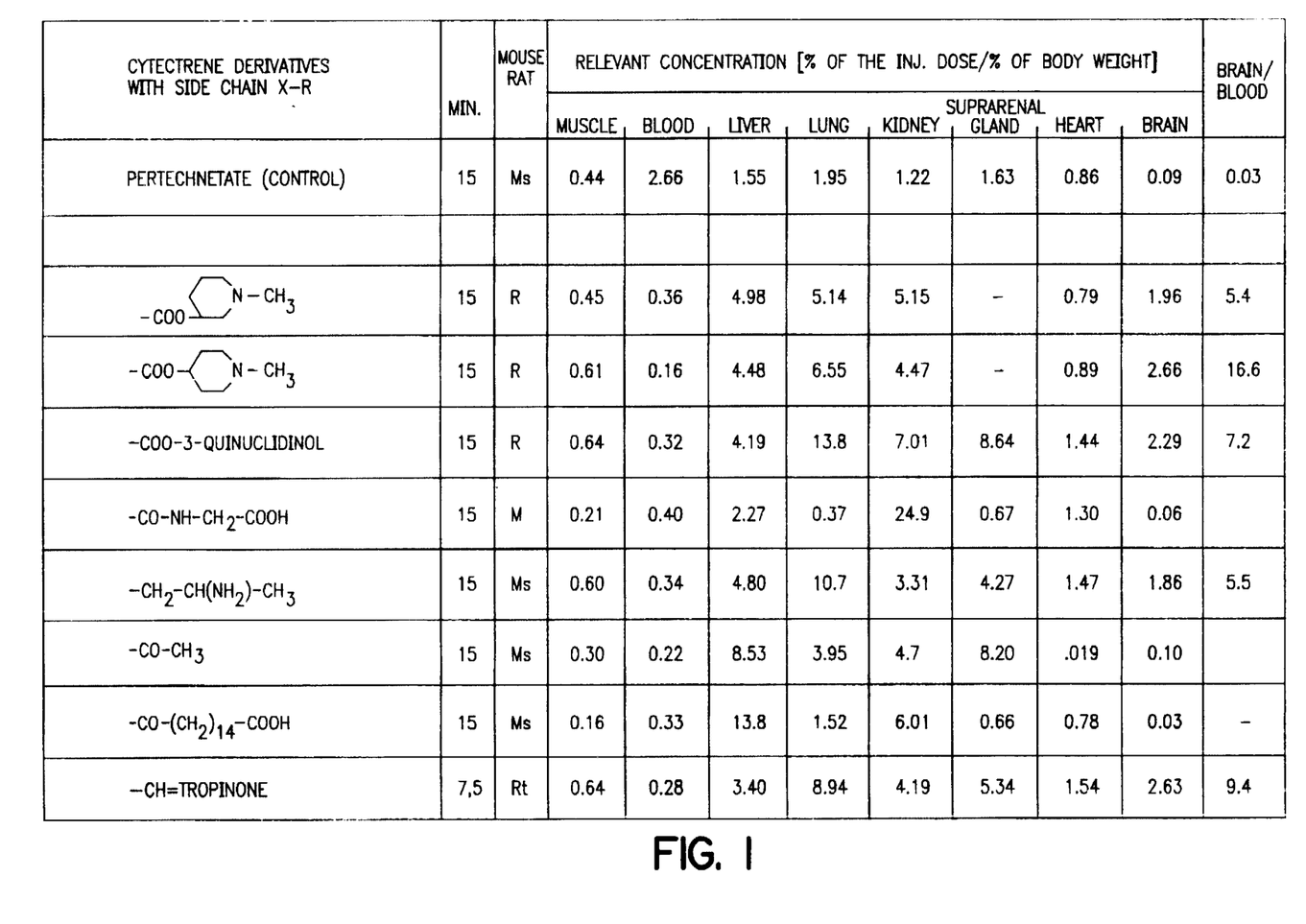
FIG. 1 is a table listing organ distribution of cytectrene derivatives.

FIG. 1 indicates the organ distribution of various cytectrene derivatives. For comparison, the organ distribution of pertechnetate was also recorded in this table. From the organ concentrations, it can clearly be recognized that the organ distribution of the cytectrene derivatives drastically differs from the distribution after administration of pertechnetate. With pertechnetate, the organ with the highest radioactivity concentration is blood (2.6% of dose/% body weight). On the other hand, the $^{99m}$Tc cytectrene derivatives show a pronounced affinity for other, respectively different organs. The affinity for the individual organ is clearly dependent on the side chain of the cytectrene compound.

Examples for practical uses result in the Hippuran-analogous cytectrene compound for kidney diagnosis and the esters with quinuclidinol or 4-hydroxy-(N-methyl)-piperidine for brain representation.

Figure 2:
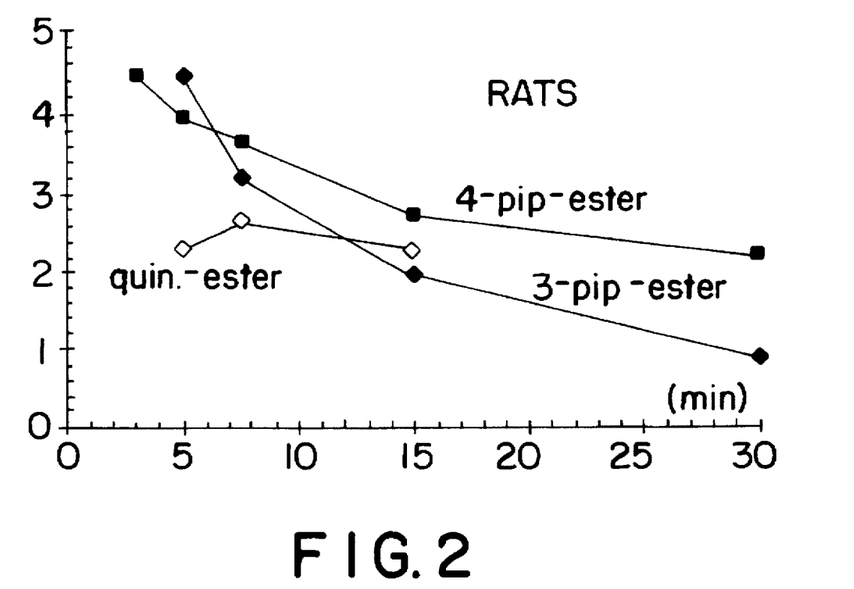
FIG. 2 illustrates test results for the concentration of $^{99m}$Tc complexes in rat brains.
Figure 3:
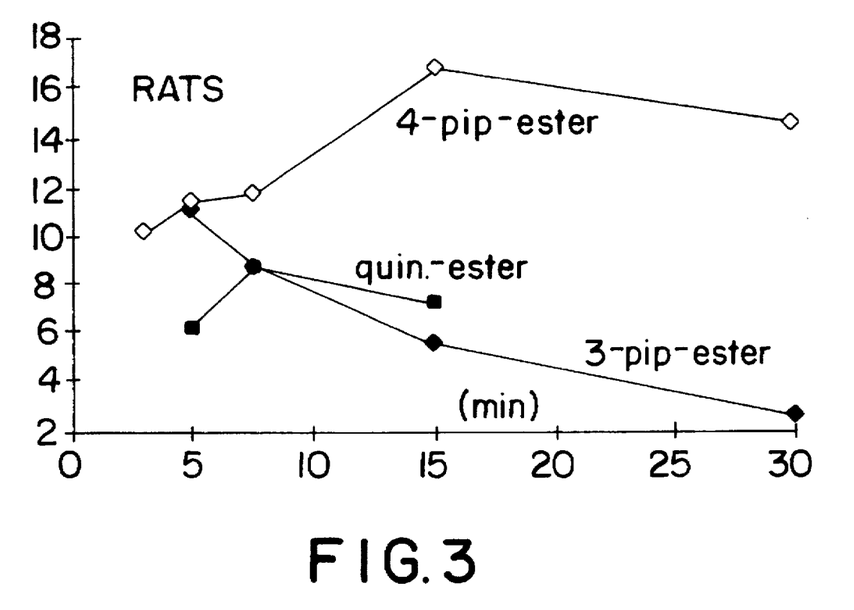
FIG. 3 illustrates test results of the brain/blood concentration ratio of $^{99m}$Tc complexes in rat brains.

FIG. 2 graphically illustrates the results of tests on $^{99m}$Tc concentration in the brain (% dose/% weight). In the experiments, the rats (n=4) intravenously received about 5 μCi of the Tc-99-labeled ester dissolved in 0.1 ml of EtOH/0.9% NaCl per animal. The esters, i.e., 4-pip-ester, 3-pip-ester and quin.-ester, were obtained from cytectrene-carboxylic acid and the following, respectively: 4-hydroxy-N-(methyl)-piperidine, 3-hydroxy-N-(methyl)-piperidine and 3-quinuclidinol. 15 minutes after HM-PAO administration, the brain concentration is at 1.7% dose/% weight. FIG. 3 shows the $^{99m}$Tc-concentration quotient brain/blood. The rats (n=4) intravenously received about 5 μCi of the Tc-99-labeled ester dissolved in 0.1 ml of EtOH/0.9% NaCl per animal. The esters tested were obtained from cytectrenecarboxylic acid and 4-hydroxy-N-(methyl)-piperidine, 3-hydroxy-N-(methyl)-piperidine and 3-quinuclidinol, respectively. 15 minutes after HM-PAO administration, the brain/blood quotient is at 1.5:1.

Thus, tests on the rat (see FIGS. 2 and 3) showed that the concentration in the brain, e.g., for the cyclopentadienylcarboxylic acid-(N-methyl-piperidinol)-4-ester- $^{99m}$technetium-tricarbonyl complex (produced analogously to example 6), is about 4% dose/% body weight, while comparable measurements for known compounds, such as, e.g., the HM-PAO complexes, yielded values around 1.7% dose/% body weight (L. Bacciottini et al., Europ. J. Nucl. Med., 17 (1990) 242. Further, the concentration ratio of brain/blood is better approximately by the factor 10.

These results were able to be confirmed by comparative studies on rabbits after administration of 14 MBq of said compound according to the invention, with a comparable amount of the HM-PAO complex relative to the activity (see experimental part) and are expressed in a more clearly visual delimitability of the brain in SPECT tests.

SYNTHESIS

The process according to the invention first offers access to the $^{99m}$Tc-labeled radiodiagnostic agents of cytectrene type according to the invention with an unlimited multiplicity for side chain —XR. The production of the complexes according to the invention takes place by $^{99m}$Tc-pertechnetate being reacted with a neutrally or positively charged cyclopentadienyl compound, carrying substituent —XR, of iron, chromium or cobalt of general formula III or IV (III)

(IV)

in which M stands for iron, chromium or cobalt, and —XR has the mentioned meaning, in the presence of a carbonyl group donor such as, e.g., $Mn(CO)_5Br$, $Fe_2(CO)_9$ or sodium formate, preferably $[FeCp(CO)_2]_2$ or oxalic acid, optionally by adding a reducing agent, such as, e.g., tin(II) chloride, hydrazine, dithionite or sodium thiosulfate, preferably in a solvent—which optionally can be acidiffied with, e.g., hydrochloric acid—such as, e.g., tetrahydrofuran, methanol, ethanol or their aqueous mixtures, optionally by adding a catalyst such as, e.g., thallium cyclopentadienyl, thallium acetate, magnesium chloride or cyclopentadienyl titanium dichloride in a closed vessel or in the melt at temperatures between 50° and 210° C., preferably at 120°–170° C.

The addition of reducing agents is generally necessary in the case of the previously known processes to reduce the $^{99m}$Tc-pertechnetate (oxidation stage +7) accumulating as generator eluate to an oxidation stage suitable for incorporation in the complex (in the case of the compounds according to the invention +1). Surprisingly, in the case of ferrocene derivatives, the addition of a separate reducing agent in the process according to the invention is often superfluous, since the used metallocene itself can act as reducing agent.

Under the carbonyl donors, those are preferred which are manganese-free, such as, e.g., $[FeCp(CO)_2]$ or oxalic acid.

The use of these donors makes possible the "vehicle-free" production of the cytectrenes according to the invention. By "vehicle-free" is to be understood that the desired $^{99m}$Tc-technetium complex is not contaminated by complexes with the same ligands but other central atoms. These often undesirable analogous manganese complexes can be formed in the use of manganese-containing carbonyl donors in a secondary reaction. A separation of these by-products, e.g., with the help of a silica gel column, is not possible in the case of manganese because of similar $R_f$ values, or only with expense unacceptable for clinical use.

With the addition of receptors, these by-products enter into competition with the radioactive species or displace the $^{99m}$Tc-technetium complex from its binding site.

The synthesis and separation of vehicle-free $^{99m}$Tc-cytectrene derivatives thus represents a decisive advantage relative to the usual—produced in clinical practice—"vehicle-free" $^{99m}$Tc complexes. In the preformulated small glasses used for this purpose, the complexing agent (chelate) is namely present in excess in an amount of 0.5–2 mg, which forms a vehicle-free technetium complex after $^{99m}$Tc-pertechnetate addition. Endogenous ions can also form an analogous complex with the unused excess of chelating agents, a complex which is similarly bound by the receptor to be tested, such as the radioactive complex. This means: Ion complexes formed in the body itself can displace at least partially the technetium complex from its binding site and thus result in a reduced $^{99m}$Tc-concentration. Exactly this possibility is impossible in the $^{99m}$-Tc-cytectrenes produced according to the process of the invention.

By the synthesis of "vehicle-free" $^{99m}$technetium complexes, it is achieved that only the desired radioactive complex is bound to the receptors, by which first the representation of, e.g., dopamine receptors, which previously was possible only by PET or $^{123}$iodine-SPECT recording techniques, is possible.

Figure 4:
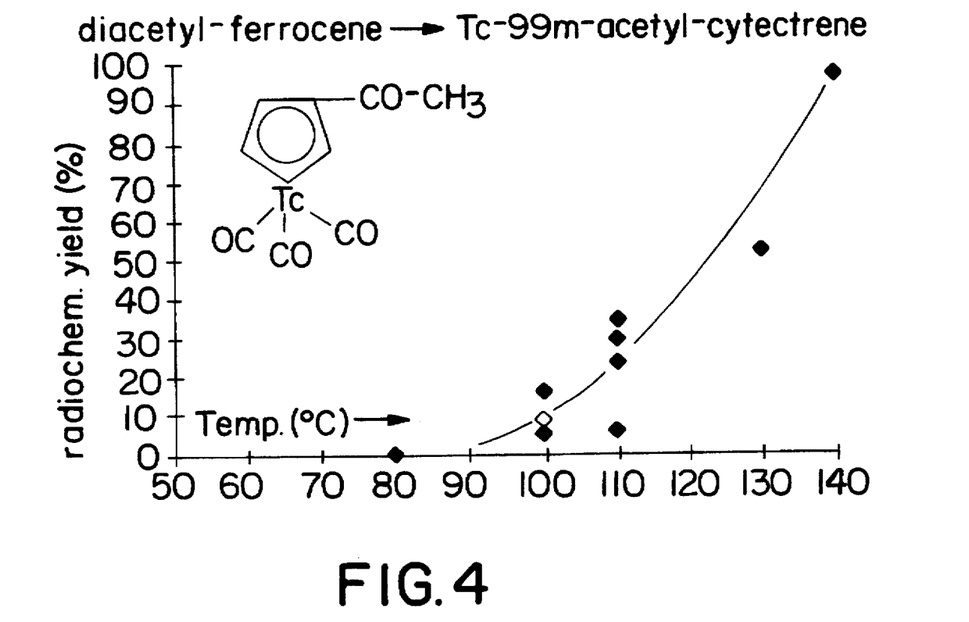
FIG. 4 illustrates $^{99m}$Tc-acetyl-cytectrene yield as a function of reaction temperature.

As tests showed, the preferred reaction temperature for this central atom exchange lies in the range between 120°–170° C. This is documented, e.g., by FIG. 4, which shows the radiochemical yield of the compound produced according to example 1 (central atom exchange Fe→$^{99m}$Tc). These temperatures can be achieved in clinical practice, e.g., in a vapor pressure sterilizer. The reaction times are in the range of 15 to 60 minutes.

A separation of the technetium-labeled compound of radioactive by-products and non-radioactive companion substances is to be achieved in the simplest way by thin-layer chromatography or HPLC. But, this is often also possible with the help of a small silica gel column, which is charged with the reaction batch and then eluted with various eluants.

The production of the pharmaceutical agents according to the invention takes place in a way known in the art, by the cytectrenes according to the invention—optionally by adding the additives usual in galenicals—being dissolved in water, alcohol or their mixtures and then sterilized by filtration. Suitable additives are, for example, physiologically harmless buffers (e.g., tromethamine), small additions of electrolytes (e.g., sodium chloride), stabilizers (e.g., gluconate, phosphates or phosphonates).

In nuclear medical in vivo use, the agents according to the invention are dosed in amounts smaller than $10^{-10}$ mol/kg of body weight. Starting from an average body weight of 70 kg, the amount of radioactivity for diagnostic uses is between 180–1100 MBq, preferably 500–800 MBq per administration. The administration is normally performed by intravenous, intraarterial, peritoneal or intratumoral injection of 0.1 to 2 ml of a solution of the agent according to the invention. The intravenous administration is preferred.

The following examples are used to explain the object of the invention in more detail.

EXAMPLES

MATERIAL AND METHODS

The ferrocene derivatives were for the smaller part purchasable products. However, for the most part, they were synthesized according to the data in the literature. The Tc-99m pertechnetate was the usual eluate (with physiological NaCl solution) of a molybdenum generator. The radioactive thin-layer plates were directly measured with the Berthold thin-layer scanner LB 2322.

EXAMPLE 1a

Tc-99m Acetyl-cytectrene from diacetylferrocene 3 mg of diacetylferrocene, 6 mg of $Mn(Co)_5Br$, 1 mg of $MnCl_2$, 1.5 mg of $Na_2S_2O_4$, 100 μCi of $TcO_4$— (contained in 10 μl of eluate of a Tc-generator) as well as 0.1 ml of methanol are added in a glass ampule. The scalee ampule is heated for 1 hour to 100° C.

The ampule contents are then applied to silica gel-TLC plates of the Merck company and cyclohexane/ethyl acetate (7:3) chromatographed. As a chromatogram shows, a maximum, which contains 16% of the $^{99m}$Tc-activity used, is obtained at $R_f$ 0.36.

The $R_F$ value is identical with the $R_F$ value of the Mn-containing substance formed in this connection, the acetylcymantrene, whose constitution corresponds to the following formula:

$C_5H_4$—CO—$CH_3 \cdot Mn \cdot (CO)_3$.

If the reducing agent dithionite is replaced by 0.1 mg of $SnCl_2$ in the above batch, the yield of $^{99m}$Tc-acetyl-cymantrene increases to over 60%.

This lipophilic $^{99m}$Tc-compound can be obtained in pure form by elution of the corresponding silica gel fraction ($R_F$=0.36), e.g., with ethanol. The radiochemical purity is established by rechromatography of the eluate. The labeled compound is chemically stable, since after 24 hours, no decomposition is chromatographically detectable.

The organ-distribution in mice shows a preferred concentration in liver and suprarenal glands for $^{99m}$Tc-acetylcymantrene and thus a completely different behavior in comparison to the $^{99m}$Tc-pertechnetate.

EXAMPLE 1b 3 mg of diacetylferrocene, 6 mg of $Mn(CO)_5Br$,

1 mg of $MnCl_2$, 0.1 mg of $SnCl_2$,

100 μCi of $TcO_4$—(contained in 10 μl of eluate of a Tc-generator)

as well as 0.1 ml of methanol are added in a glass ampule. The sealed ampule is heated for 1 hour to 130° C.

The ampule contents are then applied to silica gel-TLC plates of the Merck Company and cyclohexane/ethyl acetate (7:3) chromatographed. A maximum, which contains 60% of the $^{99m}$Tc-activity used, is obtained from the chromatogram at $R_F$ 0.36.

The $R_F$ value is identical with the $R_F$ value of the Mn-containing substance formed in this connection, the acetylcymentrene, whose constitution corresponds to the following formula:

$C_5H_4$—CO—$CH_3 \cdot Mn \cdot (CO)_3$ (proof by mass spectrum).

This lipophilic $^{99m}$Tc-compound can be obtained in pure form by elution of the corresponding silica gel fraction ($R_F$=0.36), e.g., with ethanol. The radiochemical purity is established by rechromatography of the eluate. The labeled compound is chemically stable, after 24 hours, no decomposition is chromatographically detectable.

EXAMPLE 2

Synthesis: Tc-99m cytectrene-CO-ergoline

The ferrocene precursor Fc-CO-6-methylergoline (Fc= ferrocenyl) was obtained from the activated ferrocenecarboxylic acid ester and 6-methylergoline.

1.5 mg of Fc-CO-6-methylergoline 4 mg of $Mn(CO)_5Br$ 1 mg of Tl-acetate in 0.2 ml of THF 20% $H_2O$ were contained in an ampule for 1 hour at 170° C.

Yield: 64%

Figure 5:
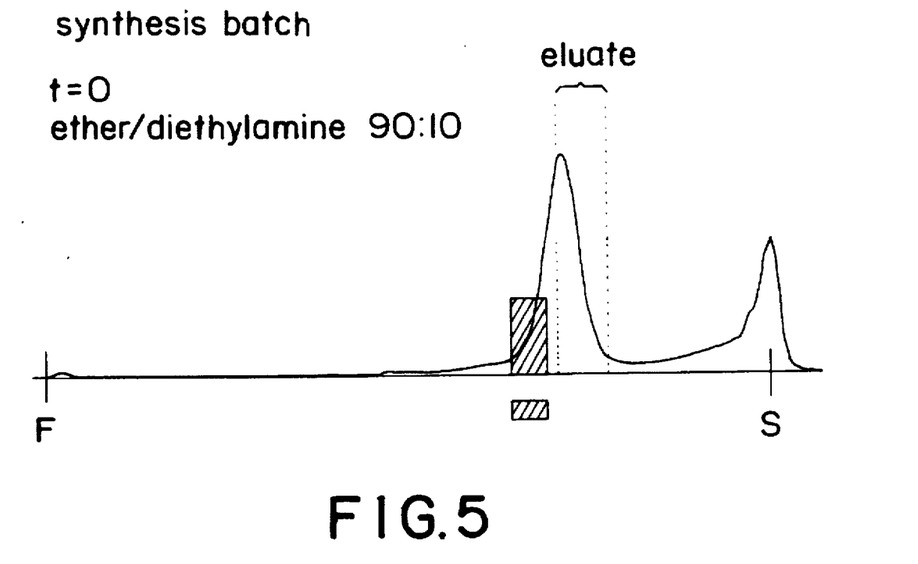
FIG. 5 illustrates a thin-layer chromatogram of the unpurified synthesis batch obtained in Example 2.
Figure 6:
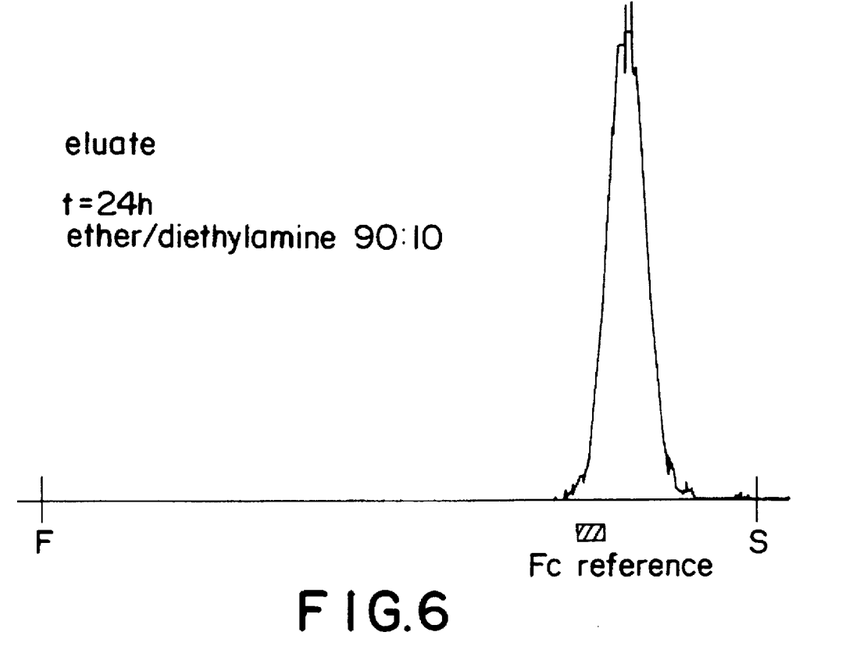
FIGS. 6 and 7 illustrate thin-layer chromatograms of purified $^{99m}$Tc-labelled compounds.
Figure 7:
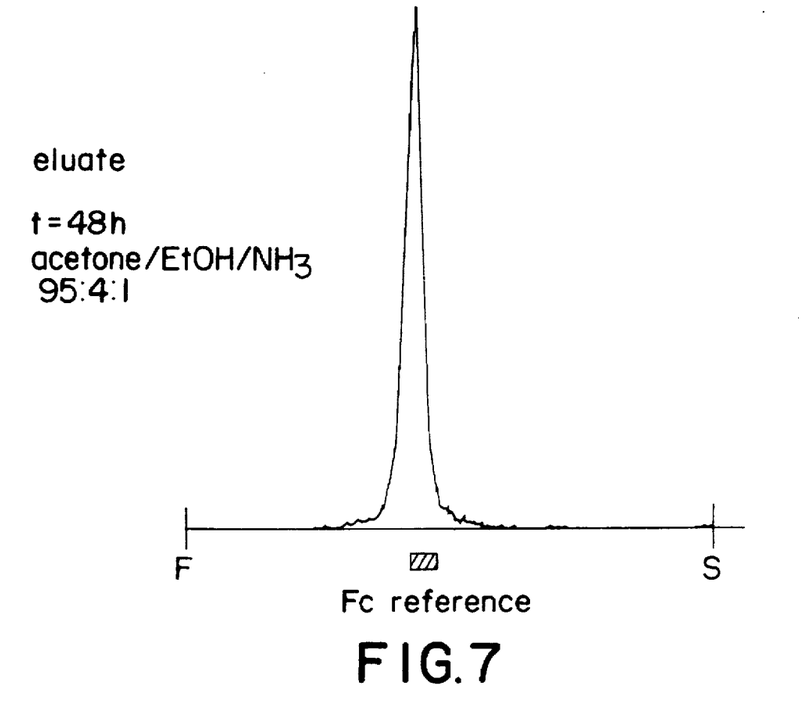

The thin-layer chromatogram of the unpurified synthesis batch, is shown in FIG. 5, the thin-layer chromatograms of the purified $^{99m}$technetium-labeled compounds are shown in FIGS. 6 and 7.

EXAMPLE 3

Tc-99m Cytectrene-CO$(CH_2)_{14}$—COOH from ferrocene—CO—$(CH_2)_{14}$—COOH 2 mg of Fc—CO—$(CH_2)_{14}$—COOH 4 mg of $Mn(CO)_5Br$ 0.2 ml of tetrahydrofuran with 30% water 0.02 ml of pertechnetate solution with 11.7 MBq are heated in a glass ampule for 1 hour to 150° C. Then, the ampule contents are quantitatively applied to a silica gel plate in streaks and chromatographed in chloroform/acetone/formic acid (75:20:1.5). The radioactive maximum with $R_F$ 0.74 (yellow coloring by the ferrocene starting product) is scraped off and this silica gel fraction is eluted with acetone. With a rechromatography in the same mobile solvent and in cyclohexane/ethyl acetate (60:40), the Tc-99m compound proves uniform; here, the $R_F$ value of 0.17 was also identical with the $R_F$ value of the ferrocene fatty acid.

Radiochem. yield: 63%

EXAMPLE 4

Tc-99m-Cytectrene-"haloperidol" from ferrocene-haloperidol a) To produce the vehicle-free cytectrene compound (see formula below), 2 mg of ferrocene-"haloperidol"

4 mg of $[FeCp(CO)_2]_2$ 1 mg of $MgCl_2 \cdot 6H_2O$ 0.2 ml of tetrahydrofuran 0.02 ml of pertechnetate solution with 0.5 MBq are heated in a glass ampule for 1 hour to 170° C. Then, TLC in ethanol/acetone/ammonia (5:95:0.5), Fc-haloperidol: $R_F$= 0.60, radiochem. yield of cytectrene-"haloperidol" ($R_F$=0.71, 41%. If 4 mg of oxalic acid is selected as carbonyl donor, the radiochem. yield is about 21%.

b) To produce the cytectrene compound (in a mixture with cymantrene-"haloperidol"), 2 mg of ferrocene-"haloperidol"

4 mg of $Mn(CO)_5Br$ 0.2 ml of ethanol 0.02 ml of pertechnetate solution with 0.7 MBq are added in a glass ampule, and the sealed ampule is heated for hour to 150° C., radiochem yield: 93% with THF as solvent 95%.

The Tc-99m cytectrene-"haloperidol" is slowly decomposed by UV light (e.g., with prolonged viewing of thin-layer chromatograms under a UV lamp).

$^{99m}$Tc-Cytectrene-Haloperidol

EXAMPLE 5

Figure 8:
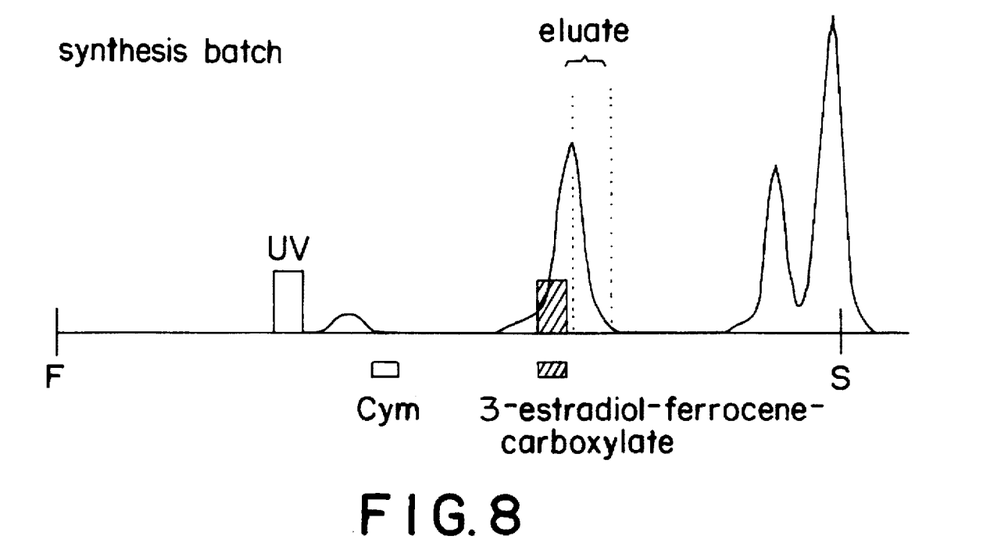
FIGS. 8 and 9 illustrate chromatograms of synthesis batch and purified $^{99m}$Tc-labelled compound obtained according to Example 5.
Figure 9:
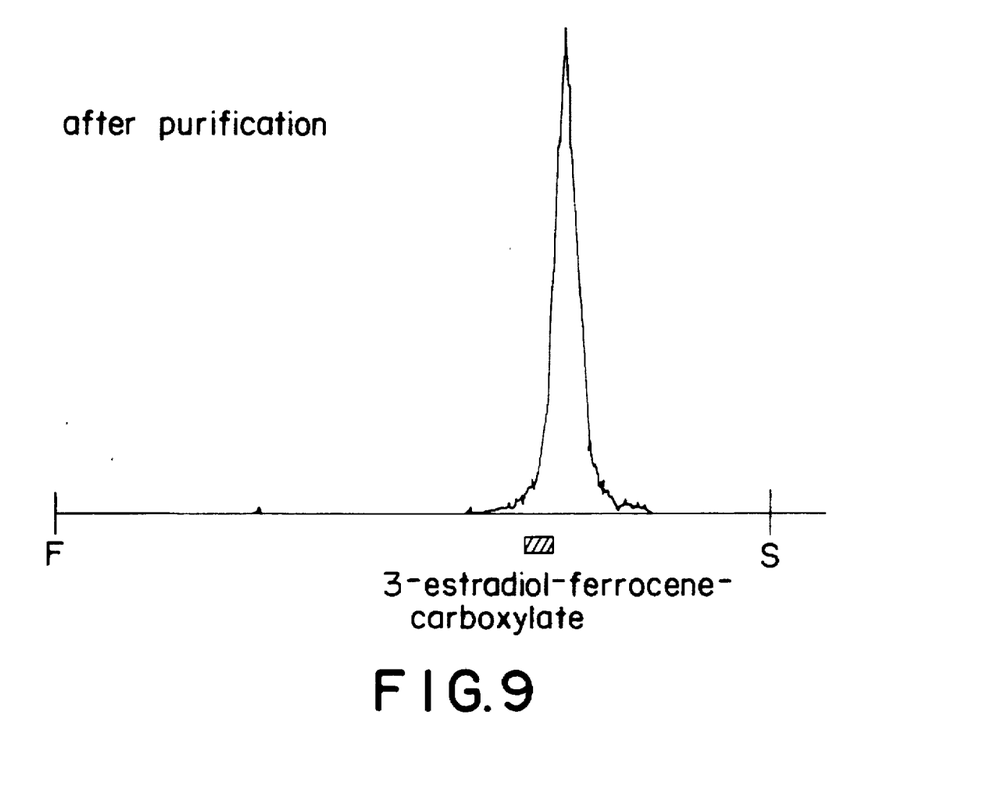

Esters of Tc-99m-cytectrenecarboxylic acid with estradiol from 3-estradiol-ferrocene-carboxylate 1 mg of 3-estradiol-ferrocene-carboxylate
2 mg of Mn(CO)$_5$Br
1 mg of Tl-acetate
0.2 ml of tetrahydrofuran with 30% water 0.02 ml of pertechnetate solution with 1.05 MBq are heated in a glass ampule for 1 hour to 170° C. TLC in cyclohexane/ethyl acetate (60:40), radiochem. yield of the cytectrene ester (R$_F$=0.33) 31%. Cf. also chromatograms FIGS. 8 and 9.

EXAMPLE 6

Tc-99m 3-Quinuclidinol-cyctectrene-carboxylate from 3-quinuclidinol-ferrocene-carboxylate 2 mg of quinuclidinol-ferrocene-carboxylate
2 mg of Mn(CO)$_5$Br
0.2 ml of tetrahydrofuran with 30% water 0.02 ml of pertechnetate solution with 1.6 MBq are heated in an ampule for 1 hour to 150° C. The ampule contents are chromatographed by TLC in ether/diethylamine (95:5).

R$_F$ of the ferrocene ester and the cytectrene esters at 0.25. Radio chem. yield: 64%.

A separation of the two esters in the mobile solvent of ethanol/acetone/NH$_3$ (5:95:0.5) is possible.

EXAMPLE 7

Tc-99m-Benzoylcytectrene from dibenzoyl-ferrocene

To each glass ampule (A and B) are added:

3 mg of dibenzoyl-ferrocene
3 mg of Mn(CO)$_5$Br
1 mg of cyclopentadienyl-thallium
0.2 ml of tetrahydrofuran with 30% water 0.02 ml of pertechnetate solution with 5 MBq of Tc-99m Ampule B contains in addition 0.5 mg of SnCl$_2$.

The sealed ampules are heated for 1 hour to 120° and the contents are then chromatographed on a silica gel thin layer plate in cyclohexane/ethyl acetate (7:3). Dibenzoyl-ferrocene: R$_F$ 0.33

Radiochem. yield of benzoyl-cytectrene (R$_F$=0.44), ampule A: 19%, ampule B: 36%

Bibliographic references for the production of the used initial compounds, as well as other $^{99m}$Tc complexes according to the invention selected as examples, can be seen from the following table.

TABLE

| Ferrocene Initial Products | | Temp. | Yield | Solvent |
|---|---|---|---|---|
| Fc(—CO-Ph)$_2$[1] | | 120° C. | 92% | MeOH |
| Fc(—CO—NH—CH$_2$—COOEt)$_2$[1] | (1) | 130° C. | 12% | MeOH + 3% HCl |
| Fc-CO—NH—CH$_2$—COOH | (1) | 150° C. | 31% | THF |
| Fc(—COOMe)$_2$[1] | | 150° C. | 25% | MeOH + 3% HCl |
| Fc(—COCH$_3$)$_2$[1] | | 140° C. | 98% | MeOH |
| Fc-CO—CH═CH-Ph | (2) | 130° C. | 45% | MeOH + 3% HCl |
| Fc-COOCH$_3$ | | 150° C. | 63% | THF + 30% H$_2$O |
| Fc-CONH$_2$ | | 150° C. | 51% | THF + 30% H$_2$O |
| Fc-CO—CH$_2$COOEt[2] | | 150° C. | 61% | THF + 30% H$_2$O |
| Fc-CO—(CH$_2$)$_2$—COOH[2] | | 150° C. | 90% | THF |
| Fc-CO—(CH$_2$)$_7$—COOH[2] | | 150° C. | 26% | EtOH |
| Fc-CO—(CH$_2$)$_{14}$—COOH | (3) | 150° C. | 69% | THF + 30% H$_2$O |
| Fc-(CH$_2$)$_{15}$—COOH | (3) | 170° C. | 29% | EtOH |
| Fc-Haloperidol | (4) | 150° C. | 95% | EtOH, THF + 30% H$_2$O |
| N-(Fc-CH$_2$—)-Glucosamine | (5) | 150° C. | 18% | THF + 30% H$_2$O |
| Fc-COO—⟨⟩—N—CH$_3$  ortho, meta | | 150° C. | 58% | THF + 30% H |
| Fc-COO-3-quinuclidinol | (6) | 150° C. | 61% | THF + 30% H$_2$O |
| Fc-COO-3-Cholesterol | (7) | 150° C. | 32% | THF + 30% H$_2$O |
| Fc-COO-3-Estradiol | (7) | 170° C. | 31% | THF + 30% H$_2$O |
| Fc-COO-17-Estradiol | (7) | 170° C. | 24% | THF + 30% H$_2$O |
| Fc-CH═CH—CO—CH$_3$ | | 170° C. | 41% | MeOH |

TABLE-continued

| Ferrocene Initial Products | | Temp. | Yield | Solvent |
|---|---|---|---|---|
| Fc-CH$_2$—CH(—NH-isopropyl)—CH$_3$ | (8) | 150° C. | 45% | THF + 30% H$_2$O |
| Fc-CH$_2$—CH(—NH-isopropyl)—C$_2$H$_5$ | (8) | 150° C. | 46% | THF + 30% H$_2$O |
| Fc-C≡CH | (10) | 170° C. | 4% | THF |
| Fc-CO—C≡CH[2)] | | 150° C. | 49% | EtOH |
| N—(Fc-CO—)-ergolinamine | | 150° C. | 65% | EtOH |
| Fc-CO—N—CH$_3$[3)] | | 170° C. | 81% | EtOH |
| Fc-CO—NN—CH$_2$—CH$_3$[3)] | | 170° C. | 75% | EtOH |
| 2-ferrocenylidene-quinuclidin-3-one | 9 | 150° C. | 40% | EtOH |
| 2-ferrocenylidene-quinuclidin-3-ol | 9 | 150° C. | 31% | THF |
| 2-ferrocenylidene-tropin-3-one | | 150° C. | 12% | MeOH |
|  | | 150° C. | 29% | EtOH |

Fc = Ferrocenyl-

The central atom exchange took place without adding SnCl$_2$ and without adding catalysts, such as, e.g., Tl-acetate or MgCl$_2$ (see examples).

The bibliographic references ( ) in the table are comprised in the supporting list.

1) The formed cytectrene derivative is only monosubstituted.
2) The ferrocene initial products are obtained by reaction of ferrocene with the corresponding acid chlorides or anhydrides according to Fiedel-Craft.
3) Obtained by reaction of Fc-COCl with the corresponding amines.
4) Production of the ferrocene compound analogously to (9).

BIBLIOGRAPHY FOR THE TABLE (1) Wenzel, M., Meinhold, H. and Schachschneider, G., Eur. J. Nucl. Med. 10, 138 (1985).
(2) Dissertation of Nipper, E., FU (Free University) Berlin 1977.
(3) Private communication, J. H. Park (1988)
(4) Wenzel, M. and Wu, Y., Appl. Radiat. Isotopes 39, 1237 (1988).
(5) Schneider, M. and Wenzel, M., J. Labelled Comp. and Radiopharmac. 18, 293 (1981).
(6) Wenzel, M., J. Labelled Comp. Radiopharmac., 27, 369 (1989).
(7) Hoffmann, K., Riesselmann, B. and Wenzel, M. Liebigs Ann. Chem. 1181 (1980).
(8) Wenzel, M., Langstaedtler, M. and Preiss, D., J. Appl. Radiat. Isot. 39, 1023–1027 (1988).
(9) Wenzel, M. J. Labelled Comp. Radiopharmac. 28, 1001 (1990).
(10) Sterzo, C. and Stille, J. K., Organometallics 9, 687 (1990).

(11) N(Ferrocenyl-methylene)-2-nitro-imidazole results by reaction of bromoacetic acid with nitroimidazole; then the resulting carboxylic acid is converted to the acid chloride, which reacts with ferrocene according to Friedel-Craft to the desired product.

EXAMPLE OF AN IN VIVO STUDY

In an in vivo study on rabbits (New Zealander, breeding by Schering AG Berlin, approximately 4 kg, male), the cerebral blood flow of commercially available HM-PAO was compared with the N-methyl-piperidin- 4-ol-cytectren-ecarboxylic acid ester (produced analogously to example 6).

The study was made with a SPECT camera of Apex 409 type.

After nembutal anesthesia, the animal was intravenously administered 1 ml of an isotonic, aqueous, sterile solution of $^{99m}$Tc-HMPAO or said cytectrene derivative.

The recording technique and the results are described by the following table.

| | HM-PAO | Cytectrene |
|---|---|---|
| Recording technique: | | |
| administered activity: | 59 MBq of $^{99m}$Tc-HM-PAO | 14 MBq of $^{99m}$Tc-cytectrene |
| test period: | 2400 seconds | 2400 seconds |
| beginning of test: | 8 minutes p.i. | 15 minutes p.i. |
| recording system: | APEX 409/APC 3 | APEX 409/APC 3 |
| recording mode: | collimator | collimator |
| filtering: | step and shoot | step and shoot |
| zoom factor: | Hanning HN 0-1-1 | Hanning HN 0-1-1 |
| matrix size: | 2 | 2 |
| | 64 × 64 pixel$^2$ | 64 × 64 pixel$^2$ |

| | HM-PAO | Cytectrene |
|---|---|---|
| Results: | | |
| cerebral uptake: | 5.9% of the administered activity | 7.5% of the administered activity |
| contrast [brain/background]: | 0.98 | 0.98 |
| static: | 2% [(σ cts/pixel) (μcts/pixel)$^{-1}$ 100] | 1.4% [(σ cts/pixel) (μcts/pixel)$^{-1}$ 100] |

We claim:

1. A cyclopentadienylcarbonyl-$^{99m}$Tc complex of formula I (I)

wherein

X is carbonyl or a direct bond;

R is phenyl, benzyl, a saturated or unsaturated, straight-chain or branched $C_{1-16}$ hydrocarbon radical optionally containing 1–3 carbonyl groups, 1–3 carboxy groups, a $C_{1-3}$ alkyl, a phenylcarboxylic acid ester, a benzylcarboxylic acid ester, —$NR_1R_2$ or combinations thereof, —$(CH_2)_lNR_3R_4$, or an alcohol molecule minus its acidic proton;

$R_1$ and $R_2$ are each, independently, hydrogen, deuterium, straight-chain or branched $C_{1-6}$ alkyl, a desoxysaccharide radical or a desaminoergoline radical;

l is 0 or 1;

$R_3$ and $R_4$ are each, independently, hydrogen, a straight-chain or branched, saturated or unsaturated $C_{1-6}$ alkyl optionally substituted by $C_{1-3}$ alkyl, phenylcarboxylic acid ester, benzylcarboxylic acid ester, or a carboxylic acid radical;

$R_3$ and $R_4$, together with nitrogen, can also form a saturated or unsaturated 5- or 6-member ring optionally containing an oxygen atom, $NR_5$ or $CHR_5$;

$NR_3R_4$ can also be a 2-nitroimidazole radical or a biogenic amine radical;

$R_5$ is hydrogen, deuterium or a straight-chain or branched $C_{1-4}$ alkyl;

X—R can also be

,  ,

,  ,

, or

2. A compound according to claim 1, wherein R is the residue of $C_{1-6}$ alkyl alcohol, phenyl alcohol, benzyl alcohol, cyclic amine alcohol, or steroid alcohol.

3. A compound according to claim 2, wherein R is the residue of a cyclic amine alcohol and said cyclic amine alcohol is tropanol, quinuclidinol or wherein $R_6$ is hydrogen, deuterium or a straight-chain or branched $C_{1-4}$-alkyl.

4. A compound according to claim 1, herein X—R is —$(CH_2)_lNR_3R_4$, $NR_3R_4$ is a biogenic amine, and said biogenic amine is serotonin, histamine or γ-aminobutyric acid.

5. A compound according to claim 2, wherein R is the residue of asteroid alcohol and said steroid alcohol is 3-cholesterol, 3-estradiol or 17-estradiol.

6. A compound according to claim 1, wherein R is a carboxy-$C_{2-16}$ alkylene group.

7. A compound according to claim 1, wherein —X—R is —CO—CH=CH—$C_5H_6$, —CO—NH—$CH_2$COOH, —CO—$CH_2$COOEt, —CO—$(CH_2)_2$COOH, —CO—$(CH_2)_{14}$COOH, —CH=CH—CO—$CH_3$, —$CH_2$CH($NH^{iso}C_3H_7$)$CH_3$, —CH($NH^{iso}C_3H_7$)$C_2H_5$, —C≡CH, —CO—C≡CH, —CO—$(CH_2)_7$COOH.

8. A process for production of compounds of formula I (I)

wherein

X is carbonyl or a direct bond;

R is phenyl, benzyl, a saturated or unsaturated, straight-chain or branched $C_{1-16}$ hydrocarbon radical optionally containing 1–3 carbonyl groups, 1–3 carboxy groups, a $C_{1-3}$ alkyl, a phenylcarboxylic acid ester, a benzylcarboxylic acid ester, —$NR_1R^2$ or combinations thereof, —$(CH_2)_lNR^3R^4$, or the residue of an alcohol molecule;

$R_1$ and $R_2$ are each, independently, hydrogen, deuterium, straight-chain or branched $C_{1-6}$ alkyl, a desoxysaccharide radical or a desaminoergoline radical;

l is 0 or 1;

$R_3$ and $R_4$ are each, independently, hydrogen, a straight-chain or branched, saturated or unsaturated $C_{1-6}$ alkyl optionally substituted by $C_{1-3}$ alkyl, phenylcarboxylic acid ester benzylcarboxylic acid ester, or a carboxylic acid radical;

R$_3$ and R$_4$, together with nitrogen, can also form a saturated or unsaturated 5- or 6-member ring optionally containing an oxygen atom, NR$_5$ or CHR$_5$;

NR$_3$R$_4$ can also be a 2-nitroimidazole radical or a biogenic amine radical;

R$_5$ is hydrogen, deuterium or a straight-chain or branched C$_{1-4}$ alkyl; or X—R is

[chemical structures]

said process comprising:

reacting $^{99m}$pertechnetate with a complex of a cyclopentadienyl moiety and iron, chromium or cobalt, said cyclopentadienyl moiety carrying substituent —X—R, in the presence of a carbonyl group donor optionally with addition of a reducing agent, optionally with addition of a catalyst in a closed vessel or in a melt at temperatures of 50°–210° C.

9. In a radiodiagnostic method comprising administering a $^{99m}$Tc compound to a subject, the improvement wherein said $^{99m}$Tc compound is a cyclopentadienylcarbonyl- $^{99m}$Tc complex according to claim 1.

10. A pharmaceutical composition comprising a cyclopentadienylcarbonyl- $^{99m}$Tc complex according to claim 1 and a carrier.

11. A process for production of pharmaceutical compositions according to claim 10, comprising dissolving said complex in water, alcohol or a water-alcohol mixture, optionally with conventional galenic additives and sterilizing the resultant solution.

12. A composition according to claim 10, wherein the radioactivity exhibited by the composition is 180–1100 MBq of $^{99m}$Tc.

13. A kit for production of cyclopentadienylcarbonyl- 99mTc complexes according to claim 1, said kit comprising:

a reaction vessel sealed with a septum, said reaction vessel containing a complex of a cyclopentadienyl moiety and iron, chromium or cobalt, said cyclopentadienyl moiety carrying the substituent —X—R, a carbonyl group donor, optionally a reducing agent, and optionally a catalyst in sterile form.

14. A compound according to claim 1, wherein said residue of an alcohol is a residue of a C$_{1-6}$-alkyl alcohol, formyl alcohol, benzyl alcohol, cyclic amine alcohol, or steroid alcohol, and said biogenic amine is serotonin, histamine or γ-aminobutyric acid.

15. A compound according to claim 1, wherein —NR$_3$R$_4$ is pyrrole, pyrazole, pyrazine, pyridine, morpholine, pyrrolidine, pyrimidine, piperidine, piperazine, 4-R$_5$-piperidine, or N-R$_5$-piperazine, and R$_5$ is a straight-chain or branched C$_{1-4}$-alkyl.

16. A compound according to claim 15, wherein R$_5$ is methyl, ethyl, propyl or isopropyl.

17. A process according to claim 8, wherein said carbonyl group donor is Fe$_2$(CO)$_9$, [FeCp(CO)$_2$]$_2$, oxalic acid, sodium formate or Mn(CO)$_5$Br, said reducing agent is tin(II) chloride, hydrazine, dithionite or sodium thiosulfate, and said catalyst is thallium cyclopentadienyl, magnesium chloride, cyclopentadienyl titanium dichloride or thallium acetate.

18. A process according to claim 8 wherein said reaction is conducted in a solvent.

19. A method according to claim 9, wherein said cyclopentadienylcarbonyl- $^{99m}$Tc complex is administered in an amount of 500–800 MBq per 70 kg.

20. A composition according to claim 12, wherein the radioactivity exhibited by said composition is 500–800 MBq of $^{99m}$Tc.

21. A kit according to claim 13, further comprising a pertechnetate solution.

22. A compound according to claim 1, wherein said cyclic amine alcohol is a cyclic aliphatic aminoalcohol.

23. A composition according to claim 10, wherein said carrier is water, alcohol, or mixtures thereof.

24. A compound according to claim 1, wherein

X is carbonyl;

R is phenyl, benzyl, a saturated or unsaturated, straight-chain or branched C$_{1-16}$ hydrocarbon radical optionally containing 1–3 carbonyl groups, 1–3 carboxy groups, a C$_{1-3}$ alkyl, a phenylcarboxylic acid ester, a benzylcarboxylic acid ester, —NR$_1$R$_2$ or combinations thereof, —(CH$_2$)$_l$NR$_3$R$_4$, or an alcohol molecule minus its acidic proton;

R$_1$ and R$_2$ are each, independently, hydrogen, deuterium, straight-chain or branched C$_{1-6}$ alkyl, a desoxysaccharide radical or a desaminoergoline radical;

l is 0 or 1;

R$_3$ and R$_4$ are each, independently, hydrogen, a straight-chain or branched, saturated or unsaturated C$_{1-6}$ alkyl optionally substituted by C$_{1-3}$ alkyl, phenylcarboxylic acid ester, benzylcarboxylic acid ester, or a carboxylic acid radical;

R$_3$ and R$_4$, together with nitrogen, can also form a saturated or unsaturated 5- or 6-member ring optionally containing an oxygen atom, NR$_5$ or CHR$_5$;

NR$_3$R$_4$ can also be a 2-nitroimidazole radical or a biogenic amine radical;

R$_5$ is hydrogen, deuterium or a straight-chain or branched C$_{1-4}$ alkyl;

X—R can also be

[chemical structures]

25. A compound according to claim 1, wherein
X is carbonyl or a direct bond;
R is phenyl, benzyl, or an alcohol molecule minus its acidic proton;

$R_1$ and $R_2$ are each, independently, hydrogen, deuterium, straight-chain or branched $C_{1-6}$ alkyl, a desoxysaccharide radical or a desaminoergoline radical;

l is 0 or 1;

$R_3$ and $R_4$ are each, independently, hydrogen, a straight-chain or branched, saturated or unsaturated $C_{1-6}$ alkyl optionally substituted by $C_{1-3}$ alkyl, phenylcarboxylic acid ester, benzylcarboxylic acid ester, or a carboxylic acid radical;

$R_3$ and $R_4$, together with nitrogen, can also form a saturated or unsaturated 5- or 6-member ring optionally containing an oxygen atom, $NR_5$ or $CHR_5$;

$NR_3R_4$ can also be a 2-nitroimidazole radical or a biogenic amine radical;

$R_5$ is hydrogen, deuterium or a straight-chain or branched $C_{1-4}$ alkyl;

X—R can also be

26. A process according to claim 8, wherein said reaction is conducted in an acidified solvent.

27. A cyclopentadienylcarbonyl-$^{99m}$Tc complex of formula I (I)

wherein
X is carbonyl or a direct bond;
R is a saturated or unsaturated, straight-chain or branched $C_{1-16}$ hydrocarbon radical containing —$NR_1,R_2$, and optionally containing 1–3 carbonyl groups, 1–3 carboxy groups, a $C_{1-3}$ alkyl, a phenylcarboxylic acid ester, a benzylcarboxylic acid or combinations thereof, or an alcohol molecule minus its acidic proton, wherein said alcohol molecule is a cyclic amine alcohol or steroid alcohol;

one of $R_1$· and $R_2$· is a desoxysaccharide radical or a desaminoergoline radical and the other is hydrogen, deuterium or straight-chain or branched $C_{1-6}$ alkyl; is 0 or 1;

one of $R_3$ and $R_4$ is a straight-chain or branched, saturated or unsaturated $C_{1-6}$ alkyl substituted by phenylcarboxylic acid ester, benzylcarboxylic acid ester, or a carboxylic acid radical and the other is hydrogen, a straight-chain or branched, saturated or unsaturated $C_{1-6}$ alkyl optionally substituted by $C_{1-3}$ alkyl, phenylcarboxylic acid ester, benzylcarboxylic acid ester, or a carboxylic acid radical;

$R_3$ and $R_4$, together with nitrogen, can also form a saturated or unsaturated 5- or 6-member ring optionally containing an oxygen atom, $NR_5$ or $CHR_5$;

$NR_3R_4$ can also be a 2-nitroimidazole radical or a biogenic amine radical;

$R_5$ is hydrogen, deuterium or a straight-chain or branched $C_{1-4}$ alkyl;

X—R can also be

28. A compound according to claim 1, wherein R is an alcohol molecule minus its acidic proton wherein said alcohol molecule is cyclic amine alcohol or steroid alcohol.

29. A compound according to claim 1, wherein R is —$(CH_2)_lNR_3R_4$ and $NR_3R_4$ is a 2-nitroimidazole or a biogenic amine radical.

30. A compound according to claim 1, wherein X—R is

, or

31. A compound according to claim 28, wherein said cyclic amine alcohol is of the formula wherein
$R_5$ and $R_6$ are each, independently, $C_{1-4}$-alkyl.

* * * * *